United States Patent [19]

Boré et al.

[11] 4,089,942

[45] May 16, 1978

[54] DEODORANT COMPOSITION AND PROCESS

[75] Inventors: Pierre Boré, Montfermeil; Jean-Claude Arnaud; Arnaud de Labbey, both of Paris, all of France

[73] Assignee: L'Oreal, Paris, France

[21] Appl. No.: 762,330

[22] Filed: Jan. 25, 1977

[30] Foreign Application Priority Data

Jan. 29, 1976 Luxembourg ............................ 74266

[51] Int. Cl.² ................................................. A61K 7/32
[52] U.S. Cl. ................................ 424/47; 424/DIG. 5; 424/65
[58] Field of Search ................ 424/47, 68, 65, DIG. 5

[56] References Cited

U.S. PATENT DOCUMENTS

| | | | |
|---|---|---|---|
| 2,210,014 | 8/1940 | Teller | 424/65 X |
| 2,230,082 | 1/1941 | Montenier | 424/68 |
| 2,230,084 | 1/1941 | Montenier | 424/65 X |
| 2,236,387 | 3/1941 | Wallace, Jr. et al. | 424/65 X |
| 2,246,524 | 6/1941 | Kyrides | 424/65 X |
| 2,828,265 | 3/1958 | Van Strien | 424/DIG. 5 |
| 2,900,306 | 8/1959 | Slater | 424/65 |
| 3,124,506 | 3/1964 | Holman | 424/65 X |
| 3,141,821 | 7/1964 | Compeau | 424/65 |
| 3,198,828 | 8/1965 | Matter | 424/65 X |
| 3,949,087 | 4/1976 | Bacq et al. | 424/365 |
| 4,005,189 | 1/1977 | Reese | 424/DIG. 5 |
| 4,010,254 | 3/1977 | Koulbanis et al. | 424/365 |

*Primary Examiner*—Dale R. Ore
*Attorney, Agent, or Firm*—Cushman, Darby & Cushman

[57] ABSTRACT

A deodorant composition which prevents the formation of unpleasant odors due to bacterial decomposition of perspiration comprises a cosmetic carrier and, as the active component, a mixture of at least one weak organic acid and at least one salt of a weak organic acid and an aminated organic compound. The composition on application to the desired area of the body maintains the pH of the perspiration at a value of about 3 to 6.

16 Claims, No Drawings

DEODORANT COMPOSITION AND PROCESS

The present invention relates to a cosmetic deodorant composition as well as to a process to prevent or substantially suppress the formation of unpleasant odors due to bacterial decomposition of perspiration by applying the said compositions to the axillary, inguinal and interdigital areas of the body.

Heretofore, and apart from odor absorbing molecules, two principal classes of products designed to combat against unpleasant odors caused by human perspiration have been known.

The first of these products are anti-perspiration compositions which act to block or greatly limit the secretion of perspiration and are based on astringents such as aluminum salts, and principally aluminum hydroxy chloride. These anti-perspirant compositions prevent the formation of unpleasant odors by directly supressing the secretion of perspiration by the skin.

The second of these products are compositions which do not all, or only slightly, alter the volume of perspiration secreted. However, because of their antiseptic or bactericidal effect they destroy bacteria which is the source of perspiration decomposition.

Representative materials having such deodorizing characteristics include hexachlorophene, bithionol (bisphenol), quaternary ammonium compounds such as "Cequartyl" and certain ion exchange resins or 1,3-diketone metallic chelates.

The compositions belonging to these two classes do not, however, provide total satisfaction. For instance, the astringent based or anti-perspiration compositions inhibit the natural secretion of perspiration and they exhibit additionally an unfavorable action on the skin. Further, the bactericidal type compositions have been found inconvenient since they totally destroy the microbial flora of the skin, thereby undesirably disturbing the biologic equilibrium of the skin.

It has now surprisingly been found that it is possible to prevent or significantly suppress the malodorous decomposition of perspiration by the action of microorganisms, without requiring the use of either astringent materials such as those which are used in anti-perspirant compositions or bactericidal substances which totally modify the microbial flora of the skin.

The present invention thus relates to a deodorant composition for body hygiene containing, in an appropriate cosmetic carrier, essentially as the active component, a mixture consisting of at least one weak organic acid and at least one salt of a weak organic acid and an aminated organic compound, the said weak organic acid having the empirical formula: $C_nH_m(OH)_x(COOH)_y$, wherein $n$ is 0 or a whole number from 1 to 6, $m$ is a whole number from 1 to 8, $x$ is 0, 1 or 2 and $y$ is 1, 2 or 3, and having a molecular weight not exceeding 192; the said mixture on application to the skin maintaining the pH of the perspiration at a value approximately fixed between about 3 to 6.

It has been shown, by tests, that the use of such compositions, based on this said mixture, prevent or substantially suppress the formation of unpleasant odors without, however, perceptibly modifying the bacterial flora present on the skin.

In other words, the composition according to the present invention has a selective action on those bacteria which are essentially responsible for the bacterial degradation of the perspiration, which degradation leads to the formation of unpleasant odors.

Consequently, the compositions according to the present invention do not appreciably disturb the biologic equilibrium of the skin, which heretofore could not be avoided with the use of known deodorant compositions based principally on a wide spectrum of bactericidal agents including, for example, hexachlorophene.

It has also now been found that the use of, as the active component, a mixture of a weak organic acid and a salt of a weak organic acid and an aminated organic compound, permits the production of excellent cosmetic formulations. In effect, the constituents of the said active component mixture exhibit excellent solubility in conventional cosmetic solvents thereby facilitating the attainment of a wide variety of formulations without experiencing such undesirable phenomena, as for example, a precipitation of the active component.

Representative weak organic acids usefully employed in the said active component mixture and which correspond to the empirical formula given above, include, particularly, formic acid, acetic acid, citric acid, maleic acid, lactic acid, tartaric acid, adipic acid, phthalic acid, salicylic acid and succinic acid.

Representative aminated organic compounds employed to form the salt present in said active component mixture are compounds having a primary, secondary or tertiary amine function. These aminated organic compounds can be mono- or pluri-functional compounds and include, for instance, amino alcohols, amino acids or aminated polymers. Optionally, these aminated compounds can be heterocycles. Representative aminated compounds include, particularly:

(1) amino alcohols such as 2-amino-2-methyl propanol-1, 2-amino-2-methyl-1,3-propanediol, monoethanolamine, diethanolamine, triethanolamine or mono-, di- and triisopropanolamines;

(2) amino acids such as histidine, arginine, lysine and ornithine;

(3) aminated polymers such as cationic polymers resulting from the condensation of piperazine, epichlorohydrin and diglycolamine or polyoxyethylenated or polyoxypropylenated fatty amines; or (4) compounds such as ortho tolylbiguanidine or S-benzyl cysteamine or one of their salts of a weak organic acid.

As indicated above, the compositions according to the present invention after having been applied to the skin and after the removal of the volatile components thereof and/or having been mixed with perspiration maintain the pH of the perspiration at a value approximately fixed between 3 and 6.

According to the present invention, the pH transmitted to the perspiration should be lower than the pK of the acid employed in the said active component mixture of the composition. However, if the pH transmitted is higher than the pK of the said acid, the pH transmitted to the perspiration must at a maximum (1) be only 0.8 unit higher when the pK of the acid is between 3 and 4.5, or (2) only 0.5 unit higher when the pK of the acid is between 4.5 and 5, or (3) only 0.2 unit higher when the pK of the acid is between 5 and 6.

Generally, the most favorable results are achieved when the pH transmitted to the perspiration has approximately the same value as the pK of the acid employed in the said active component mixture.

The effectiveness of this said mixture is greater as the pH imparted to the perspiration is closer to 3. From a cosmetic point of view, a pH of 3 is considered an acceptable limit for good tolerance with the mucous membranes of the skin and principally with those of the axillary, inguinal and interdigital areas of the body.

The deodorant compositions according to the present invention can be provided under various forms and particularly in the form of an aqueous solution containing, optionally, a certain amount of alcohol, it being understood however that the said active component mixture is soluble in the cosmetic carrier selected.

The compositions according to the present invention can also comprise a solution of the said active component mixture in a volatile liquid, such as alcohol, which rapidly evaporates after application of the said composition on the skin. Preferably, the compositions according to the present invention are provided as an aerosol and are packaged in an aerosol container under pressure and in the presence of a liquified gaseous propellant such as trichlorofluoromethane and dichlorodifluoromethane and their mixtures.

In accordance with a variation of this embodiment of the invention, the gaseous propellant employed can be carbon dioxide gas or nitrous oxide, either alone or in admixture with the above mentioned halogenated hydrocarbons. Further, other propellants can be used without departing from the present invention.

The alcohols usefully employed in the compositions of the present invention are, preferably, ethanol and isopropanol.

In yet another embodiment of the present invention, the deodorant compositions can be provided in the form of an oil-in-water or water-in-oil emulsion, the aqueous phase of said emulsion containing the said active component mixture.

Representative oils which can comprise the oil phase of the emulsion can include, particularly, (a) a hydrocarbon oil as paraffin oil, Purcellin oil ($C_8$–$C_{18}$ fatty acid esters), perhydrosqualene and a solution of microcrystalline wax in an oil;

(b) animal or vegetable oil such as sweet almond oil, avocado oil, calophylum oil, lanolin, castor oil, horse oil, hog oil, olive oil and turnsole oil;

(c) mineral oil having an initial distillation point, at atmospheric pressure, of about 250° C and a final distillation point of about 410° C; and (d) a saturated ester such as isopropyl palmitate, $C_3$–$C_{16}$ alkyl myristates such as isopropyl, butyl and cetyl myristates, hexadecyl stearate, ethyl palmitate, triglyceride of octanoic and decanoic acids, cetyl ricinoleate and $C_1$–$C_{16}$ alkyl adipates and sebacates.

In the oil phase it is also possible to use silicone oils soluble in other oils such as dimethylpolysiloxane, methylphenylpolysiloxane and the copolymer of silicone and glycol.

The compositions of the present invention can also be provided in the form of gels or sticks. The sticks comprise soaps dissolved in ethyl alcohol and polyols such as glycerine, propylene glycol, and an alcoholic or hydroalcoholic solution of the said active component mixture. These sticks can also be formulated from waxes, oils, fatty alcohols and emulsifying agents.

Representative emulsifying agents usefully employed in this type of composition include particularly fatty amides such as copra monoethanolamide, stearic diethanolamide and the like.

It is understood that the various forms of the present invention, i.e. an aqueous, hydroalcoholic or alcoholic solution, an emulsion, a gel, a stick or an aerosol, can contain any other conventional adjuvant generally employed in this type of composition.

It is clear that the pH conditions, mentioned above, so as to obtain the deodorant effect in accordance with the present invention, must be those which prevail after evaporation of the volatile component of the composition as applied to the skin.

Thus, for example, the composition as applied to the skin can, as indicated above, contain a significant amount of alcohol and have at the moment of use a pH outside the pH range mentioned above, provided that after evaporation of the alcohol or the volatile components from contact with the skin, the perspiration is maintained in the pH range between about 3 to 6.

The concentration of the said active component mixture in the composition can vary over sufficiently wide limits. Thus, the concentration selected can depend on such easily ascertainable factors as the solubility of the components of the mixture used in the composition or on the method of applying the composition to the desired area of the body. It should be clear, however, that the concentration of the active component mixture in the perspiration determines the effectiveness of the composition and not necessarily the concentration of the said mixture in the composition, per se. It will also be recognized that the concentration of the active component mixture in the perspiration depends, for instance, on the amount of composition applied to the desired area of the body and on the volume of perspiration secreted over a given period of time.

Generally, when the pK of the acid employed in said mixture is lower or equal to 5, the concentration of the acid must be at least equal to $10^{-2}M$, when the pH of the solution is lower than the pK or does not exceed the latter by more than 0.2 units, while the concentration of the acid must be at least equal to $0.5 \times 10^{-1}M$ when the pH exceeds the pK by more than 0.2 unit.

When the pK of the acid is greater than 5, the concentration of acid must be at least equal to $0.5 \times 10^{-1}M$.

Generally, the active component mixture is present in an amount between 0.5 and 15 percent by weight relative to the total weight of the composition.

The present invention also relates to a process for preventing or substantially inhibiting the formation of unpleasant odors due to bacterial decomposition of perspiration, said process comprising applying to the axillary, inguinal and interdigital areas of the body an effective amount of the composition of the present invention, as described above, so as to maintain the pH of the perspiration at a value between about 3 to 6 for a prolonged period of time. Generally the deodorant effect obtained by the composition of the present invention is maintained for a period of at least about 24 hours.

As illustrated in the accompanying examples, the salt of the weak organic acid and the aminated organic compound can be obtained in situ during the admixture of the various components of the composition or it can optionally be prepared separately, as for example in the case of s-benzylcysteamine malate.

The following non-limiting examples are given to illustrate the present invention. Unless otherwise specified, all parts and percentages are by weight.

EXAMPLE 1

In accordance with the present invention, a deodorant composition, in the form of an alcoholic spray, is prepared by admixing the following components:

| | |
|---|---|
| Acetic acid | 0.53 g |
| 2-amino-2-methyl-1,3 propanediol | 0.44 g |
| Perfume | 0.5 g |
| Ethyl alcohol, absolute, q.s.p. | 30 g |

The above admixture is then packaged under pressure in an aerosol container in the presence of:

| | |
|---|---|
| Trichlorofluoromethane | 42 g |
| Dichlorodifluoromethane | 28 g |

This composition, when applied to the underarm area and after evaporation of the volatile component thereof maintains the pH of the perspiration at 4.9 and thus prevents formation of unpleasant odors.

The above example is repeated except that the acetic acid is replaced by an essentially equivalent amount of adipic acid.

EXAMPLE 2

In accordance with the present invention, a deodorant alcoholic spray is prepared by admixing the following components:

| | |
|---|---|
| Lactic acid | 0.79 g |
| 2-amino-2-methyl-propanol-1 | 0.39 g |
| Perfume | 0.5 g |
| Ethyl alcohol, absolute, q.s.p. | 30 g |

This admixture is then packaged under pressure in an aerosol container in the presence of:

| | |
|---|---|
| Trichlorofluoromethane | 42 g |
| Dichlorodifluoromethane | 28 g |

The resulting composition, when applied to the underarm area and after evaporation of the volatile fraction thereof, maintains the pH of the perspiration at 4.2, thus preventing bacterial degradation of the perspiration.

The above example is repeated except that the lactic acid is replaced with an essentially equivalent amount of salicylic acid.

EXAMPLE 3

In accordance with the present invention, a deodorant hydroalcoholic spray is prepared by admixing the following components:

| | |
|---|---|
| Tartaric acid | 30 g |
| Monoethanolamine | 19.9 g |
| Perfume | 5 g |
| Water | 200 ml |
| Ethanol, q.s.p. | 1000 ml |

The above admixture, packaged in a container is then saturated with nitrous oxide under a pressure of 7 kg/cm².

The resulting composition, when applied to the underarm area and after evaporation of the volatile fraction thereof, maintains the pH of the perspiration at 4.3 and thus prevents the formation of unpleasant odors for a prolonged period.

The above example is repeated except that the tartaric acid is replaced by an essentially equivalent amount of formic acid.

The above example is again repeated except that the monoethanolamine is replaced by an essentially equivalent amount of monoisopropanolamine.

EXAMPLE 4

In accordance with the present invention, a deodorant lotion is prepared by admixing the following components:

| | |
|---|---|
| Citric acid, monohydrate | 42 g |
| Cationic polymer resulting from the condensation of piperazine, epichlorohydrin and diglycolamine, (28.7% aqueous solution, described in French Patent 74.27030) or its counterpart U.S. Pat. No. 4,013,387 | 180 ml |
| Ethanol | 200 ml |
| Perfume | 1 g |
| Water, q.s.p. | 1000 ml |

This lotion when applied to the underarm area and after evaporation of the volatile fraction thereof maintains the pH of the perspiration at 5.

EXAMPLE 5

In accordance with the present invention, a deodorant hydroalcoholic spray is prepared by admixing the following components:

| | |
|---|---|
| Malic acid | 26.8 g |
| Diethanolamine | 30.6 g |
| Water | 200 ml |
| Perfume | 5 g |
| Ethanol | 1000 ml |

The above mixture, packaged in a dispenser, is then saturated with $CO_2$ under a pressure of 7 kg/cm².

The resulting composition, when applied to the soles of the feet and after evaporation of the volatile fraction thereof maintains the pH of the perspiration at 3.9.

The above example is repeated except that the diethanolamine is replaced by an essentially equivalent amount of di-isopropanolamine.

EXAMPLE 6

In accordance with the present invention, a deodorant alcoholic spray is prepared by admixing the following components:

| | |
|---|---|
| Succinic acid | 1.04 g |
| Triethanolamine | 1.76 g |
| Perfume | 0.5 g |
| Ethyl alcohol, absolute, q.s.p. | 30 g |

The above mixture is then packaged under pressure in an aerosol container in the presence of:

| | |
|---|---|
| Trichlorofluoromethane | 42 g |
| Dichlorodifluoromethane | 28 g |

This spray, when applied to the underarm area and after evaporation of the volatile portion thereof, maintains the pH of the perspiration at 5.1.

The above example is repeated except that the triethanolamine is replaced by an essentially equivalent amount of tri-isopropanolamine.

EXAMPLE 7

In accordance with the present invention, a deodorant lotion for manual spraying is prepared by admixing the following components:

| | |
|---|---|
| Tartaric acid | 30 g |
| Ortho tolylbiguanidine | 70 g |
| Perfume | 5 g |
| Water | 350 ml |
| Ethanol, q.s.p. | 1000 ml |

This composition after application to the underarm area of the body and evaporation of the volatile fraction thereof maintains a pH of the perspiration at 4.5.

EXAMPLE 8

In accordance with the present invention, a deodorant hydroalcoholic spray is prepared by admixing the following components:

| | |
|---|---|
| Lactic acid | 18 g |
| Amine with a fatty chain (copra) polyoxy propylenated with 2 moles of ethylene oxide, sold under the mark "Propomeen $C_{12}$" | 29.8 g |
| Perfume | 5 g |
| Water | 100 ml |
| Ethanol, q.s.p. | 1000 ml |

This mixture, packaged in a dispenser, is then saturated with nitrous oxide under a pressure of 7 kg/cm$^2$.

The resulting alcoholic spray after application to the desired area of the body and after evaporation of the volatile fraction thereof maintains the pH of the perspiration at 3.75.

EXAMPLE 9

In accordance with the present invention a deodorant lotion for manual spraying is prepared by admixing the following components:

| | |
|---|---|
| Lactic acid | 18 g |
| Arginine | 15.5 g |
| Perfume | 1 g |
| Water | 150 ml |
| Ethanol, q.s.p. | 1000 ml |

This lotion when applied to the underarm area and after evaporation of the volatile portion thereof maintains the pH of the perspiration at 3.85, thus avoiding the formation of unpleasant odors during the 24 hour period following said application.

EXAMPLE 10

In accordance with the present invention, a deodorant hydroalcoholic spray is prepared by admixing the following components:

| | |
|---|---|
| Malic acid | 13.4 g |
| S-benzyl cysteamine malate | 19.3 g |
| Perfume | 5 g |
| Water | 100 ml |
| Ethanol, q.s.p. | 1000 ml |

This mixture, packaged in a dispenser, is then saturated with nitrous oxide under pressure of 7 kg/cm$^2$.

This spray when applied to the underarm area and after evaporation of the volatile fraction thereof maintains the pH of the perspiration at 3.4.

EXAMPLE 11

In accordance with the present invention, a deodorant emulsion is prepared from an admixture of the following components:

| | |
|---|---|
| Lactic acid | 2.11 g |
| 2-amino-2-methyl-propanol-1 | 0.9 g |
| Propylene glycol | 23.5 g |
| Cetyl stearyl alcohol polyoxyethylenated with 15 moles of ethylene oxide | 28 g |
| Cetyl alcohol | 4.7 g |
| Paraffin oil | 11.7 g |
| Isopropyl myristate | 4.7 g |
| Water | 23.54 g |

This emulsion when applied to the underarm area maintains the pH of the perspiration at 4.0.

EXAMPLE 12

In accordance with the present invention, a deodorant lotion is prepared by admixing the following components:

| | |
|---|---|
| Lactic acid | 18 g |
| L-lysine | 14.6 g |
| Ethanol | 700 ml |
| Perfume | 1 g |
| Water, q.s.p. | 1000 ml |

This lotion, after manual spraying on the underarm area and after evaporation of the volatile fraction thereof, maintains the pH of the perspiration at 3.9.

EXAMPLE 13

In accordance with the present invention, a deodorant lotion is prepared by admixing the following components:

| | |
|---|---|
| Acetic acid | 12 g |
| L-ornithine | 13.2 g |
| Ethanol | 800 ml |
| Perfume | 1 g |
| Water, q.s.p. | 1000 ml |

This lotion, after manual spraying on the underarm area and after evaporation of the volatile portion thereof, maintains the pH of the perspiration at 5.1.

EXAMPLE 14

In accordance with the present invention, a deodorant lotion is prepared by admixing the following components:

| | |
|---|---|
| O-phthalic acid | 33.2 g |
| L-histidine | 48.4 g |
| Water | 500 ml |
| Perfume | 1 g |
| Ethanol, q.s.p. | 1000 ml |

This lotion, when applied to the underarm area and after evaporation of the volatile fraction thereof, maintains the pH of the perspiration at 4.8.

EXAMPLE 15

In accordance with the present invention, a deodorant lotion for manual spraying is prepared by admixing the following components:

| | |
|---|---|
| Lactic acid | 9 g |
| S-benzyl cysteamine malate | 19,3 g |
| Perfume | 1 g |
| Water | 100 ml |
| Ethanol, q.s.p. | 1000 ml |

This lotion when sprayed to the inderarm aera and after evaporation of the volatile portion thereof maintains the pH of the perspiration at 3.4, thus avoiding the formation of unpleasant odors.

EXAMPLE 16

In accordance with the present invention a deodorant lotion for manual spraying is prepared by admixing the following components:

| | |
|---|---|
| O-phthalic acid | 16,6 g |
| Arginine lactate | 26,2 g |
| Perfume | 1 g |
| Water | 150 ml |
| Ethanol, q.s.p. | 1000 ml |

This lotion when sprayed to the underarm area and after evaporation of the volatile fraction thereof maintains the pH of the perspiration at 3.2.

EXAMPLE 17

In accordance with the present invention a deodorant gel is prepared by admixing the following components:

| | |
|---|---|
| Succinic acid | 23,6 g |
| Monoethanolamine | 6,1 g |
| Hydroxy ethyl cellulose | 45 g |
| Water, q.s.p. | 1000 ml |

This gel when applied to the underarm area maintains the pH of the perspiration at 4,6, thus avoiding the formation of unpleasant odors during 24 hours period following said application.

What is claimed is:

1. A deodorant composition for body hygiene to prevent the formation of unpleasant odors due to bacterial decomposition of perspiration, comprising a cosmetic carrier and essentially as the active component in said composition a mixture of at least one weak organic acid and at least one salt of a weak organic acid and an aminated organic compound, said weak organic acid having the formula $C_nH_m(OH)_x(COOH)_y$ wherein $n$ is 0 or a whole number from 1 to 6, $m$ is a whole number from 1 to 8, $x$ is 0, 1 or 2 and $y$ is 1, 2 or 3 and having a molecular weight not exceeding 192, the said mixture on application to the selected areas of the body maintains the pH of the perspiration at a value approximately fixed between about 3 to 6.

2. The composition of claim 1 wherein said weak organic acid is selected from the group consisting of formic acid, acetic acid, citric acid, malic acid, lactic acid, tartaric acid, adipic acid, phthalic acid, salicylic acid and succinic acid.

3. The composition of claim 1 wherein said aminated organic compound is a mono- functional compound or pluri-functional compound having a primary, secondary or tertiary amine function.

4. The composition of claim 1 wherein said aminated organic compound is an amino alcohol selected from the group consisting of 2-amino-2-methyl propanol-1, 2-amino-2-methyl-1,3-propanediol, monoethanolamine, diethanolamine, triethanolamine and mono- isopropanolamine di-isopropanolamine and tri-isopropanolamine.

5. The composition of claim 1 wherein said aminated organic compound is an amino acid selected from the group consisting of histidine, arginine, lysine and ornithine.

6. The composition of claim 1 wherein said aminated organic compound is a cationic polymer resulting from the condensation of piperazine, epichlorohydrin and diglycolamine, polyoxyethylenated fatty amine or polyoxypropylenated fatty amine.

7. The composition of claim 1 wherein said organic aminated compound is ortho-tolylbiguanidine, S-benzyl cysteamine or the salt thereof with a weak organic acid.

8. The composition of claim 1 wherein the pH transmitted to the perspiration is approximately equal to the pK of the weak organic acid present in said active component mixture.

9. The composition of claim 1 wherein said active component mixture is present in an amount from 0.5 to 15 percent by weight relative to the total weight of said composition.

10. The composition of claim 1 wherein said cosmetic carrier is water, a hydroalcoholic solution or an alcohol.

11. The composition of claim 10 wherein said cosmetic carrier is an alcohol in admixture with a liquified gaseous propellant and said composition is packaged under pressure in an aerosol container.

12. The composition of claim 10 wherein said alcohol is ethanol or isopropanol.

13. The composition of claim 1 provided in the form of an oil-in-water emulsion or a water-in-oil emulsion, the aqueous phase of said emulsion containing said active component mixture.

14. The composition of claim 1 provided in the form of a gel or a stick.

15. A process for preventing the formation of unpleasant odors due to bacterial decomposition of perspiration, comprising applying to the axillary, inguinal or interdigital areas of the body, an effective deodorant amount of the composition of claim 1 so as to maintain the pH of the perspiration at a value between about 3 to 6 for a prolonged period of time.

16. The process of claim 15 wherein the pH of the perspiration is maintained at a value between 3 to 6 for a period of at least 24 hours.

* * * * *